US009735366B2

(12) United States Patent
Turchanin

(10) Patent No.: US 9,735,366 B2
(45) Date of Patent: Aug. 15, 2017

(54) HETEROSTRUCTURE COMPRISING A CARBON NANOMEMBRANE

(71) Applicant: CNM Technologies GmbH, Bielefeld (DE)

(72) Inventor: Andrey Turchanin, Bielefeld (DE)

(73) Assignee: CNM TECHNOLOGIES GMBH, Bielefeld (DE)

( * ) Notice: Subject to any disclaimer, the term of this patent is extended or adjusted under 35 U.S.C. 154(b) by 0 days.

(21) Appl. No.: 14/501,874

(22) Filed: Sep. 30, 2014

(65) Prior Publication Data

US 2016/0093806 A1    Mar. 31, 2016

(51) Int. Cl.
*H01L 29/06* (2006.01)
*H01L 31/00* (2006.01)
(Continued)

(52) U.S. Cl.
CPC .......... *H01L 51/0045* (2013.01); *B32B 9/007* (2013.01); *G01N 27/4146* (2013.01);
(Continued)

(58) Field of Classification Search
CPC .......... H01L 27/14692; H01L 29/0665; H01L 29/0669; H01L 29/413; H01L 31/035227; H01L 31/03845; H01L 51/0045; H01L 51/0048; H01L 51/057; H01L 51/426; H01L 51/4266; H01L 51/444; H01L 51/502; H01L 2224/05193; H01L 2224/05293; H01L 2224/05393; H01L 2224/05493; H01L 2224/05693; H01L 2224/05793; H01L 2224/05893; H01L 2224/05993; H01L 2224/13193; H01L 2224/13293; H01L 2224/13393; H01L 2224/13493; H01L 2224/13693; H01L 2224/13793; H01L 2224/13893; H01L 2224/37993; H01L 2224/45193; H01L 2224/45293; H01L 2224/45393; H01L 2224/45493; H01L 2224/45693;
(Continued)

(56) References Cited

U.S. PATENT DOCUMENTS 6,764,758 B1    7/2004    Grunze et al.
9,222,907 B2 *  12/2015   Prasad ............... G01N 27/3278
                                                              204/403.03
(Continued)

OTHER PUBLICATIONS

Stine, R., Mulvaney, S. P., Robinson, J. T., Tamanaha, C. R. & Sheehan, P. E. Fabrication, Optimization, and Use of Graphene Field Effect Sensors. Analytical Chemistry 85, 509-521, (2013).
(Continued)

*Primary Examiner* — Teresa M Arroyo
(74) *Attorney, Agent, or Firm* — 24IP Law Group; Timothy R DeWitt

(57) ABSTRACT

A heterostructure comprising at least one carbon nanomembrane on top of at least one carbon layer, a method of manufacture of the heterostructure, and an electronic device, a sensor and a diagnostic device comprising the heterostructure. The heterostructure comprises at least one carbon nanomembrane on top of at least one carbon layer, wherein the at least one carbon nanomembrane has a thickness of 0.5 to 5 nm and the heterostructure has a thickness of 1 to 10 nm.

10 Claims, 9 Drawing Sheets

(51) Int. Cl.

| | | |
|---|---|---|
| B05D 5/12 | (2006.01) | |
| B05D 3/00 | (2006.01) | |
| B05D 3/06 | (2006.01) | |
| C08J 7/18 | (2006.01) | |
| B32B 27/32 | (2006.01) | |
| H01L 51/00 | (2006.01) | |
| H01B 13/00 | (2006.01) | |
| B32B 9/00 | (2006.01) | |
| H01L 51/05 | (2006.01) | |
| G01N 27/414 | (2006.01) | |
| B01J 20/28 | (2006.01) | |
| H01L 31/107 | (2006.01) | |
| H01L 29/778 | (2006.01) | |
| C01B 3/00 | (2006.01) | |
| G11C 13/02 | (2006.01) | |
| H01F 1/00 | (2006.01) | |

(52) U.S. Cl.
CPC ..... *H01B 13/0026* (2013.01); *H01L 51/0046* (2013.01); *H01L 51/0096* (2013.01); *H01L 51/0545* (2013.01); *H01L 51/0562* (2013.01); *B01J 20/28007* (2013.01); *B32B 2457/00* (2013.01); *C01B 3/0021* (2013.01); *G01N 27/4145* (2013.01); *G11C 13/025* (2013.01); *H01F 1/0081* (2013.01); *H01L 29/7786* (2013.01); *H01L 31/1075* (2013.01); *H01L 2224/80493* (2013.01); *H01L 2924/13061* (2013.01); *H01L 2924/13064* (2013.01)

(58) Field of Classification Search
CPC ... H01L 2224/45793; H01L 2251/5369; H01L 2924/10325; H01L 2924/10361; H01L 2924/1308; H01L 2924/13086; H01L 2924/13088; H01L 2924/13089; H01L 2924/15793; H01L 2924/16178; H01L 2924/16593; H01L 2924/16793; H01L 2924/17793; H01L 2221/1094; H01L 21/02601; H01L 21/02603; H01L 21/02606; H01L 21/3142; H01L 51/0046; H01L 51/0096; H01L 51/0545; H01L 51/0562; H01L 2924/13064; H01L 2924/13061; H01L 29/7786; H01L 31/1075; H01L 2224/80493; H01L 2224/45893; H01L 2224/45993; H01L 2224/488; H01L 2224/29993; H01L 2224/37193; H01L 2224/37293; H01L 2224/37393; H01L 2224/37493; H01L 2224/37693; H01L 2224/37793; H01L 2224/37893; B32B 2457/00; B32B 9/007; G01N 27/4145; G01N 27/4146; H01B 13/0026; H01F 1/0081; B01J 20/28007; C01B 3/0021; G11C 13/025
USPC ....... 257/798, E51.04, 26, 27; 977/700, 742, 977/788, 590, 825, 842, 963; 427/122, 427/551; 428/220
See application file for complete search history.

(56) References Cited

U.S. PATENT DOCUMENTS

| | | | | |
|---|---|---|---|---|
| 2006/0228287 A1* | 10/2006 | Zettl | ............. | B82Y 30/00 423/447.1 |
| 2006/0292870 A1* | 12/2006 | Pribat | ............. | B01J 21/04 438/680 |
| 2007/0256941 A1* | 11/2007 | Prasad | ............. | G01N 27/3278 205/775.5 |
| 2008/0157235 A1* | 7/2008 | Rogers | ............. | H01L 21/02628 257/415 |
| 2008/0160858 A1* | 7/2008 | Paolucci | ............. | B01D 67/0058 442/349 |
| 2008/0186495 A1* | 8/2008 | Prasad | ............. | G01N 27/3278 356/440 |
| 2010/0102245 A1* | 4/2010 | Jiang | ............. | H01J 1/34 250/396 R |
| 2010/0189881 A1* | 7/2010 | Patibandla | ............. | H01G 9/016 427/77 |
| 2010/0209330 A1 | 8/2010 | Goelzhaeuser et al. | | |
| 2010/0239488 A1* | 9/2010 | Zettl | ............. | B82B 3/00 423/447.1 |
| 2010/0317124 A1* | 12/2010 | Kim | ............. | B82Y 15/00 436/149 |
| 2011/0031566 A1* | 2/2011 | Kim | ............. | B81C 1/00158 257/419 |
| 2011/0210415 A1* | 9/2011 | Altavilla | ............. | G01K 7/186 257/467 |
| 2012/0142016 A1* | 6/2012 | Ronaghi | ............. | B82Y 15/00 435/7.1 |
| 2013/0260472 A1* | 10/2013 | Holt | ............. | G01N 33/48721 436/149 |
| 2014/0293513 A1* | 10/2014 | Eilertsen | ............. | H01G 9/042 361/528 |
| 2014/0326902 A1* | 11/2014 | Tahan | ............. | H01L 49/006 250/493.1 |
| 2014/0329050 A1* | 11/2014 | Gu | ............. | G02B 6/1225 428/135 |
| 2014/0376158 A1* | 12/2014 | Kim | ............. | H01G 11/24 361/502 |

OTHER PUBLICATIONS

Wu, S. X., He, Q. Y., Tan, C. L., Wang, Y. D. & Zhang, H. Graphene-Based Electrochemical Sensors. Small 9, 1160-1172, (2013).
Kuila, T. et al. Chemical functionalization of graphene and its applications. Progress in Materials Science 51, 1061-1105, (2012).
Mao, H. Y. et al. Manipulating the electronic and chemical properties of graphene via molecular functionalization. Progress in Surface Science 88, 132-159, (2013).
Balandin, A. A. Thermal properties of graphene and nanostructured carbon materials, Nature Materials 10, 569-581, (2011).
Dreyer, D.R., Park, S., Bielawski, C. W. & Ruoff, R. S. The chemistry of graphene oxide. Chemical Society Reviews 39, 228-240, (2010).
Steenackers, M. et al. Polymer Brushes on Graphene. Journal of the American Chemical Society 133, 10490-10498, (2011).
Bekyarova, E. et al. Chemical Modification of Epitaxial Graphene: Spontaneous Grafting of Aryl Groups . . . Journal of the American Chemical Society 131, 1336-1337, (2009).
Xu, Y. X. et al. Chemically Converted Graphene Induced Molecular Flattening of 5,10,15,20-Tetrakis(I-methyl-4-pyridinio)porphyrin and Its Application for Optical Detection of Cadmium(II) Ions. Journal of the American Chemical Society 131, 13490-13497, (2009).
Turchanin, A. & Golzhauser, A. Carbon nanomembranes from self-assembled monolayers: Functional surfaces without bulk. Progress in Surface Science 87, 108-162, (2012).
Angelova, P. et al. A Universal Scheme to Convert Aromatic Molecular Monolayers into Functional Carbon Nanomembranes. ACS Nano 7, 6489-6497, (2013).
Nottbohm, C. T., Turchanin, A., Beyer, A., Stosch, R. & Golzhauser, A. Mechanically Stacked 1-mn-Thick Carbon Nanosheets: Ultrathin Layered Materials with Tunable Optical, Chemical, and Electrical Properties. Small 7, 874-883, (2011).
Li, X. S. et al. Large-area synthesis of high-quality and uniform graphene films on copper foils. Science 324, 1312-1314,(2009).
Turchanin, A. et al. Molecular mechnisms of electron-induced cross-linking in aromatic SAMs. Langmuir 25, 7342-73 52, (2009).
Eck, W. et al. Generation of surface amino groups on aromatic self-assembled monolayers by low energy electron beams—A first step towards chemical lithography. Advanced Materials 12, 805-808, (2000).

(56) References Cited

OTHER PUBLICATIONS

Schnietz, M. et al. Chemically functionalized carbon nanosieves \\-ith 1-nm thickness. Small 5, 2651-2655, (2009).
Turchanin, A. et al. One nanometer thin carbon nanosheets with tunable conductivity and stiffness. Advanced Materials 21, 1233-1237, (2009).
Pirkle, A. et al. The effect of chemical residues on the physical and electrical properties of chemical vapor deposited graphene transferred to SiO2. Applied Physics Letters 99, 122108, (2011).
Zheng, Z. et al. Janus Nanomembranes: A Generic Platform for Chemistry in Two Dimensions. Angewandte Chemie-International Edition 49, 8493-8497, (2010).
Turchanin, A. et al. Molecular self-assembly, chemical lithography, and biochemical tweezers: A path for the fabrication of functional nanometer-scale protein arrays. Advanced Materials 20, 471-477, (2008).
Blake, P. et al. Making graphene visible. Applied Physics Letters 91, 063124, (2007).
Mayorov, A. S. et al. How Close Can One Approach the Dirac Point in Graphene Experimentally? Nano Letters 12, 4629-4634, (2012).
Miroslaw Woszczyna et al "All-Carbon vertical van der Waals Heterostructures: Non-destructive Functionalization of Graphene for Electronic Applications," Adv. Mat. 2014, 26, 4831-4837.

* cited by examiner

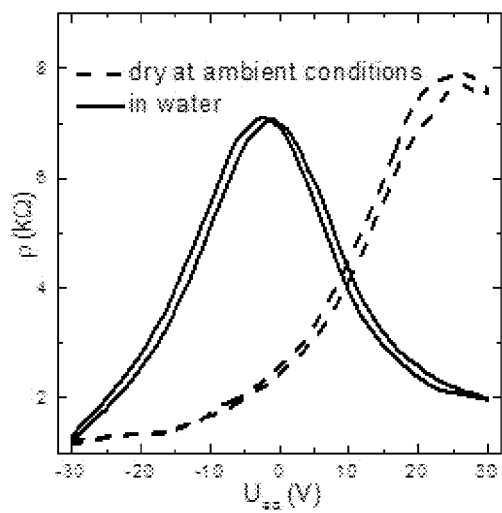 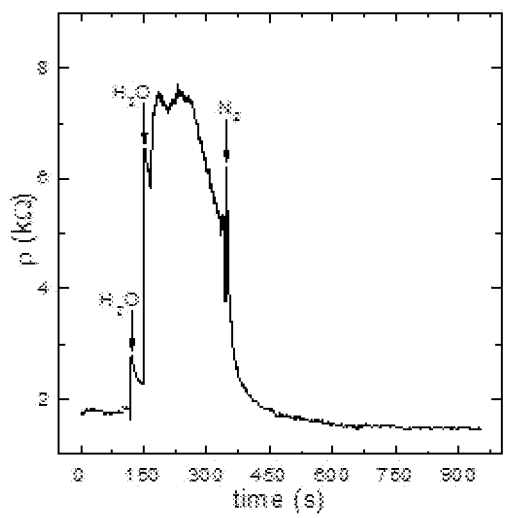
Figure 7A                    Figure 7B

HETEROSTRUCTURE COMPRISING A CARBON NANOMEMBRANE

CROSS-REFERENCE TO RELATED APPLICATIONS

None

BACKGROUND OF THE INVENTION

Field of the Invention

The invention relates to a heterostructure comprising at least one carbon nanomembrane on top of at least one carbon layer, a method of manufacture of the heterostructure, and an electronic device, a sensor and a diagnostic device comprising the heterostructure.

Brief Description of the Related Art

Functionalization of pristine carbon layers, e. g. a single layer or a few layers of graphene, allows use of the pristine carbon layers in electronic, mechanical or optical devices, e.g. as electrical transducers in electronic devices, such as, but not limited to, electric field-effect based nanosensors. Stine, R., Mulvaney, S. P., Robinson, J. T., Tamanaha, C. R. & Sheehan, P. E. Fabrication, Optimization, and Use of Graphene Field Effect Sensors. *Analytical Chemistry* 85, 509-521, (2013); Wu, S. X., He, Q. Y., Tan, C. L., Wang, Y. D. & Zhang, H. Graphene-Based Electrochemical Sensors. *Small* 9, 1160-1172, (2013). However, the pristine carbon layers have not to date been functionalized in a way which would allow their use in such devices. Kuila, T. et al. Chemical functionalization of graphene and its applications. *Progress in Materials Science* 57, 1061-1105, (2012); Mao, H. Y. et al. Manipulating the electronic and chemical properties of graphene via molecular functionalization. *Progress in Surface Science* 88, 132-159, (2013). This is because the pristine carbon layers are chemically relatively inert and are difficult to functionalize via covalent bonding. Pristine graphene is one example of a pristine carbon layer. The graphene consists of exclusively $sp^2$-carbons which are organized in a honeycomb network. A layer of fullerene is another example of a carbon layer.

Structural modifications in the pristine carbon layers can enable the functionalization by covalent bonding, but the electronic, mechanical and optical properties of the modified pristine carbon layer are diminished. Examples of the diminished electronic properties include high electrical charge mobility, strong ambipolar electric field effect, high thermal conductivity. Stine, R., Mulvaney, S. P., Robinson, J. T., Tamanaha, C. R. & Sheehan, P. E. Fabrication, Optimization, and Use of Graphene Field Effect Sensors. *Analytical Chemistry* 85, 509-521, (2013); Wu, S. X., He, Q. Y., Tan, C. L., Wang, Y. D. & Zhang, H. Graphene-Based Electrochemical Sensors. *Small* 9, 1160-1172, (2013); Kuila, T. et al. Chemical functionalization of graphene and its applications. *Progress in Materials Science* 57, 1061-1105, (2012); Mao, H. Y. et al. Manipulating the electronic and chemical properties of graphene via molecular functionalization. *Progress in Surface Science* 88, 132-159, (2013); and Balandin, A. A. Thermal properties of graphene and nanostructured carbon materials. *Nature Materials* 10, 569-581, (2011). Examples of the diminished mechanical properties include Young's modulus, internal stress and the tensile strength. Experiments have been performed with graphene as an exemplary carbon layer. Both the covalent bonding to graphene defects, as in oxidized graphene (Dreyer, D. R., Park, S., Bielawski, C. W. & Ruoff, R. S. The chemistry of graphene oxide. *Chemical Society Reviews* 39, 228-240, (2010)), or to graphene grain boundaries (Steenackers, M. et al. Polymer Brushes on Graphene. *Journal of the American Chemical Society* 133, 10490-10498, (2011)), and direct bonding to intact benzene rings (Bekyarova, E. et al. Chemical Modification of Epitaxial Graphene: Spontaneous Grafting of Aryl Groups. *Journal of the American Chemical Society* 131, 1336-1337, (2009)) were studied and have demonstrated the diminished electronic properties. In this respect, non-covalent functionalization of the carbon layers, i.e. via weak van der Waals (vdW) forces, may provide an alternative functionalization, as this non-covalent functionalization does not induce severe changes into the carbon layers, especially a change of the bonding structure. Mao, H. Y. et al. Manipulating the electronic and chemical properties of graphene via molecular functionalization. *Progress in Surface Science* 88, 132-159, (2013). Thus, the non-covalent functionalization of the carbon layers using the example of graphene with flat polyaromatic molecules like porphyrins (Xu, Y. X. et al. Chemically Converted Graphene Induced Molecular Flattening of 5,10,15,20-Tetrakis(1-methyl-4-pyridinio)porphyrin and Its Application for Optical Detection of Cadmium(II) Ions. *Journal of the American Chemical Society* 131, 13490-13497, (2009)) has been shown. The adsorbed flat polyaromatic molecules do not disrupt the carbon layer, but the stability of the flat polyaromatic molecules is low and limits use of the functionalized carbon layer in the electronic devices.

Carbon nanomembranes are a novel two-dimensional (2D) carbon-based material with dielectric properties made via electron-/photon-induced crosslinking of aromatic self-assembled monolayers. Turchanin, A. & Gölzhäuser, A. Carbon nanomembranes from self-assembled monolayers: Functional surfaces without bulk. *Progress in Surface Science* 87, 108-162, (2012); Angelova, P. et al. A Universal Scheme to Convert Aromatic Molecular Monolayers into Functional Carbon Nanomembranes. *ACS Nano* 7, 6489-6497, (2013). The carbon nanomembranes are mechanically and thermally stable. The terms "carbon nanomembrane" and "cross-linked SAMs" can be used synonymously. The carbon nanomembranes have also been described in U.S. Pat. No. 6,764,758 B1.

Structures comprising the carbon layers may be used in electronic devices, sensors or diagnostic devices. The sensors may also be the diagnostic devices. Conventional diagnostics and diagnostic devices include pathogen cultivation, PCR and enzyme immunoassays, which are all laborious, time consuming and costly methods, requiring large sample volumes, special equipment and trained staff. Mechanical, optical or magnetic sensors used for the diagnostic devices are slow and not very sensitive. Functionalization of sensor surfaces may provide molecular detection specificity in the diagnostic devices. Most capture molecules, however, are not compatible with the materials from which the sensors have been made to date. These materials include silicon, metals and graphene.

SUMMARY OF THE INVENTION

A heterostructure comprising at least one carbon nanomembrane on top of at least one carbon layer is disclosed. The at least one carbon nanomembrane has a thickness of 0.5 to 5 nm and the heterostructure has a thickness of 1 to 10 nm.

In one aspect of the disclosure, the carbon layer is a single layer of graphene or a single layer of fullerene.

In a further aspect of the disclosure, the carbon nanomembrane comprises two surfaces and at least one surface is terminated with at least one functional group.

The at least one functional group may be selected from the group consisting of halogen atoms and carboxy, trifluoromethyl, amino, nitro, cyano, thiol, hydroxy or carbonyl groups.

The at least one functional group may be an amino group.

In one aspect of the disclosure, the at least one surface of the carbon nanomembrane, which is terminated with at least one functional group, is further functionalized.

The at least one surface of the carbon nanomembrane, which is terminated with at least one functional group, may be further functionalized by at least one of a fluorescent dye, a chelator, a protein, an antibody, an oligonucleotide or a metallic nanoparticle.

The fluorescent dye may be tetramethylrhodamine or the chelator may be ethylenediaminetetraacetate.

The heterostructure may be manufactured by a method comprising the steps of
a) preparing at least one carbon nanomembrane on a substrate by the steps of
  i) providing the substrate,
  ii) adding carbon-containing compounds to a surface of the substrate,
  iii) cross-linking of the carbon-containing compounds;
b) providing at least one carbon layer;
c) separating the at least one carbon nanomembrane from the substrate;
d) stacking the at least one carbon nanomembrane on top of the at least one carbon layer.

In one aspect of the disclosure, the cross-linking comprises electron-induced or photon-induced cross-linking.

The electron-induced cross-linking may be performed at an energy of 10 to 3000 eV, preferably 20 to 300 eV, and at a charge density of at least 10 mC/cm$^2$, preferably 20 to 100 mC/cm$^2$.

The substrate may be selected from the group consisting of gold, silver, titanium, zirconium, vanadium, chromium, manganese, cobalt, tungsten, molybdenum, platinum, aluminium, iron, steel, copper, nickel, silicon, germanium, indium phosphide, gallium arsenide and oxides, nitrides or alloys or mixtures thereof, indium-tin oxide, sapphire, and silicate or borate glasses.

The carbon-containing compounds may be selected from the group consisting of phenyl, biphenyl, terphenyl, quaterphenyl, naphthaline, anthracene, bipyridine, terpyridine, thiophene, bithienyl, terthienyl, pyrrole and combinations thereof.

In one aspect of the disclosure, the carbon-containing compound is 4'-nitro-1,1'-biphenyl-4-thiol and the carbon nanomembrane is further functionalized by converting terminal nitro groups into amino groups during the cross-linking.

In another aspect of the disclosure, the method comprises an additional step e) of assembling the heterostructure on an insulating surface.

The insulating surface may be an oxidized silicon wafer with an oxide thickness of 100 to 500 nm.

In one aspect of the disclosure, the assembling is performed by a transfer medium.

At least one surface of the at least one carbon nanomembrane of the heterostructure may be terminated with at least one functional group.

An electronic device comprising a heterostructure comprising at least one carbon nanomembrane on top of at least one carbon layer, wherein the at least one carbon nanomembrane has a thickness of 0.5 to 5 nm and the heterostructure has a thickness of 1 to 10 nm, is also disclosed.

The electronic device may be a field effect transistor.

A sensor comprising a heterostructure comprising at least one carbon nanomembrane on top of at least one carbon layer, wherein the at least one carbon nanomembrane has a thickness of 0.5 to 5 nm and the heterostructure has a thickness of 1 to 10 nm, is also disclosed.

The sensor may further comprise a microfluidic system.

The sensor may be at least one of an electronic device, a MEMS device, a NEMS device, a surface plasmon resonance device, or a microbalance.

A diagnostic device comprising a heterostructure comprising at least one carbon nanomembrane on top of at least one carbon layer, wherein the at least one carbon nanomembrane has a thickness of 0.5 to 5 nm and the heterostructure has a thickness of 1 to 10 nm, is also disclosed.

BRIEF DESCRIPTION OF THE FIGURES

For a more complete understanding of the present invention and the advantages thereof, reference is now made to the following description and the accompanying drawings, in which:

FIGS. 7A and 7B show a response of the heterostructure devices to water environment.

FIG. 8A is a schematic and FIG. 8B is a graph of resistance as a function of gate voltage.

DETAILED DESCRIPTION OF THE INVENTION AND THE FIGURES

The invention will now be described in detail. Drawings and examples are provided for better illustration of the invention. It will be understood that the embodiments and aspects of the invention described herein are only examples and do not limit the protector's scope of the claims in any way. The invention is defined by the claims and their equivalents. It will be understood that features of one aspect or embodiment of the invention can be combined with the feature of a different aspect or aspects and/or embodiments of the invention.

A heterostructure comprising at least one carbon nanomembrane on top of at least one carbon layer is disclosed. The at least one carbon nanomembrane has a thickness of 0.5 to 5 nm and the heterostructure has a thickness of 1 to 10 nm. It has been surprisingly found that such thin heterostructures are very durable. At least one carbon nanomembrane assembled on top of at least one carbon layer allows functionalization of the carbon layer without significantly compromising the electronic, mechanical and optical properties of the carbon layer. The electronic properties of the carbon layers include high electrical charge mobility, strong ambipolar electric field effect and high thermal conductivity. The mechanical properties include Young's modulus, internal stress and tensile strength.

For example, the carbon nanomembrane may have a thickness of 1 nm and be placed on top of a single layer of graphene or fullerene.

Figure 1:
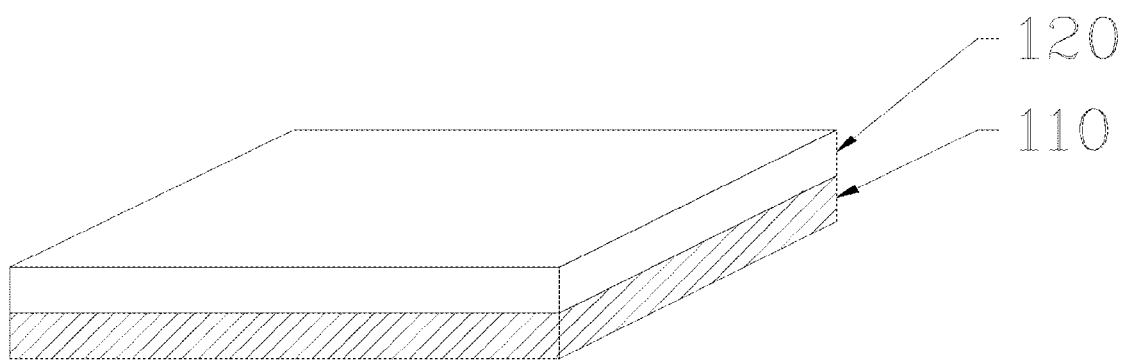
FIG. 1 is a schematic representation of a heterostructure according to the present disclosure.

FIG. 1 shows a schematic representation of a heterostructure according to the present disclosure. A carbon nanomembrane (CNM) 120 is placed on top of a carbon layer 110.

In one aspect of the disclosure, the carbon layer is a single layer of graphene. The carbon layer may also be a single layer of fullerene. The carbon layer may also be a carbon nanotube, a bilayer of graphene, a few layers of graphene, or an amorphous carbon layer.

The carbon layer is thus non-covalently functionalized by means of the carbon nanomembrane, i.e. via weak van der Waals (vdW) forces. The person ordinarily skilled in the art is aware that non-covalent functionalization by vdW forces works with every kind of carbon layer.

In a further aspect of the disclosure, the carbon nanomembrane comprises two surfaces and at least one of the two surfaces is terminated with at least one functional group. The functional group may be selected from the group consisting of halogen atoms and carboxy, trifluoromethyl, amino, nitro, cyano, thiol, hydroxy or carbonyl groups. In one aspect of the disclosure, the functional group is an amino group. The functional group does not significantly alter the thickness of the heterostructure. Thus, a heterostructure, in which at least one of the two surfaces of the carbon nanomembrane is terminated with at least one functional group, may still have a thickness of 1 to 10 nm and the carbon nanomembrane may still have a thickness of 0.5 to 5 nm.

The presence of the functional group allows further functionalization of the carbon nanomembrane. The further functionalization depends on the type of functional group with which the surface of the carbon nanomembrane is terminated. The term "further functionalization" means that, for example, at least one of a fluorescent dye, a chelator, a protein, an antibody, an oligonucleotide, or a metallic nanoparticle binds to the functional group. By way of example only, the functional group is an amino group and further functionalization is achieved by the binding of a large protein, such as the 20S proteasome, via a metal activated multivalent N-nitrilotriacetic acid chelator to the amino group. A metallic nanoparticle may be a gold nanoparticle. Further functionalization with the gold nanoparticle is, for example, possible when the CNM has been functionalized with a thiol group.

The fluorescent dye may be tetramethylrhodamine. The chelator may be ethylenediaminetetraacetate. The person ordinarily skilled in the art will be aware that many other molecules can be used for the further functionalization.

The further functionalization may significantly alter the thickness of the heterostructure, depending on the type of the further functionalization. Thus, a heterostructure, in which the carbon nanomembrane has been further functionalized, may be thicker than 1 to 10 nm and the carbon nanomembrane may be thicker than 0.5 to 5 nm.

The heterostructure may be manufactured by a method comprising the steps of
a) preparing at least one carbon nanomembrane on a substrate by the steps of
   i) providing the substrate,
   ii) adding carbon-containing compounds to a surface of the substrate,
   iii) cross-linking of the carbon-containing compounds;
b) providing at least one carbon layer;
c) separating the at least one carbon nanomembrane from the substrate;
d) stacking the at least one carbon nanomembrane on top of the at least one carbon layer.

In one aspect of the disclosure, the cross-linking comprises electron-induced cross-linking or photon-induced cross-linking. The term "cross-linking" means coupling of the adjacent phenyl rings.

The electron-induced cross-linking may be performed at an energy of 10 to 3000 eV, preferably 20 to 300 eV, and at a charge density of at least 10 mC/cm$^2$, preferably 20 to 100 mC/cm$^2$.

The carbon nanomembranes can be easily transferred and can therefore be termed "freestanding" carbon nanomembranes. The carbon nanomembranes show high mechanical strength and thermal stability. The carbon nanomembranes can be prepared as thin homogenous monolayers on a large scale, i. e. on large areas (for example larger than several square meters).

The carbon nanomembranes have a low environmental impact. The carbon nanomembranes do not include environmentally harmful or toxic components.

Many different methods are known in the state of the art to provide the at least one carbon layer. In case of graphene for example, a second substrate may be provided and low weight hydrocarbons, e. g. methane, ethane or benzene, are placed on a surface of the second substrate by a chemical vapor deposition process at high temperatures. Chemical vapor deposition (CVD) is a chemical method, which is used to produce very thin layers. The layer of graphene is then separated from the second substrate before the at least one carbon nanomembrane is stacked on top of the at least one carbon layer.

Another example for the provision of graphene is to provide a second substrate, adding carbon-containing compounds to a surface of the second substrate, cross-linking of the carbon-containing compounds, thus preparing a carbon nanomembrane on a second substrate and annealing the carbon nanomembrane.

The process of annealing of the carbon nanomembranes refers to the heating of the carbon nanomembranes under inert gas or at a reduced pressure. With further annealing, nanocrystalline graphene is formed, as described in international patent application No. WO 2009/030473.

The layer of graphene is then separated from the second substrate before the at least one carbon nanomembrane is stacked on top of the at least one carbon layer.

Graphene may also be provided by exfoliation from graphite, a chemical reduction of graphene oxide or heating silicium carbide under low pressure.

It will be noted that the graphene is only one example of the carbon layer as other types of the carbon layers may also be used. For example, a layer of fullerene may be manufactured by evaporation on a second substrate.

The heterostructure may also form stacks of at least one hetero structure. In other words, multi-heterostructures are possible which comprise at least one carbon layer-CNM-heterostructure stacked on top of one another.

The substrate may be selected from the group consisting of gold, silver, titanium, zirconium, vanadium, chromium, manganese, cobalt, tungsten, molybdenum, platinum, aluminium, iron, steel, copper, nickel, silicon, germanium, indium phosphide, gallium arsenide and oxides, nitrides or alloys or mixtures thereof, indium-tin oxide, sapphire, and silicate or borate glasses. The choice of the substrate will depend on the application.

The carbon-containing compounds may be selected from the group consisting of phenyl, biphenyl, terphenyl, quaterphenyl, naphthaline, anthracene, bipyridine, terpyridine, thiophene, bithienyl, terthienyl, pyrrole and combinations thereof. The carbon-containing compounds of the present invention are cross-linked to yield a carbon nanomembrane.

One example is the carbon nanomembrane from the carbon-containing compound 4'-nitro-1,1'-biphenyl-4-thiol. In this example, the carbon nanomembrane is further functionalized by converting terminal nitro groups into amino groups during the cross-linking.

In another aspect of the disclosure, the method comprises an additional step e) of assembling the heterostructure on an insulating surface. The insulating surface may, for example, be an oxidized silicon wafer, silicon carbide, glass, or a polymer.

For example, the insulating surface may be an oxidized silicon wafer with an oxide thickness of 100 to 500 nm.

In one aspect of the disclosure, the assembling is performed by a transfer medium. The transfer medium may comprise a photoresist. The transfer medium may be dissolved in a further processing step.

An electronic device comprising a heterostructure comprising at least one carbon nanomembrane on top of at least one carbon layer, wherein the at least one carbon nanomembrane has a thickness of 0.5 to 5 nm and the heterostructure has a thickness of 1 to 10 nm, is also disclosed.

The electronic device may be a field effect transistor.

A sensor or a diagnostic device comprising a heterostructure comprising at least one carbon nanomembrane on top of at least one carbon layer, wherein the at least one carbon nanomembrane has a thickness of 0.5 to 5 nm and the heterostructure has a thickness of 1 to 10 nm, are also disclosed.

The sensor may also be an electronic device. In other words, an electronic sensor is also disclosed. The sensing concept may be based on a field effect transistor or on metallic resistivity change.

The diagnostic devices comprising the heterostructures of the present disclosure can, for example, be used for the detection of markers in any kind of clinical setting.

The accurate measurement of chemical concentrations is not only used in clinical diagnostics, but is also needed in many industrial and security uses, such as but not limited to control of water quality, food quality, environmental monitoring, or screening for explosives. The sensors made using the functionalized carbon layers of this disclosure are highly sensitive, fast and reliable.

The sensor may further comprise a microfluidic system. A microfluidic system means that microfluidic channels for the transport of fluids are incorporated into the sensor. The sensor may also be built into an electronic-fluidic sensor package. Electrodes or other nanostructures may also be added to the electronic-fluidic sensor package. The sensor of the current disclosure thus enables the incorporation of components necessary for the sensing of a molecule in a single chip.

The sensor may be at least one of an electronic device, a micro-electro-mechanical systems (MEMS) device, a nano-electro-mechanical systems (NEMS) device, a surface plasmon resonance device, or a microbalance. Thus, the sensors may be miniaturized devices useful in many different sensing applications.

EXAMPLES

Heterostructure Comprising an Amino-Terminated Carbon Nanomembrane ($NH_2$-CNM) on Top of a Single Layer of Graphene (SLG)

An amino-terminated carbon nanomembrane ($NH_2$-CNM) has been assembled on top of a single layer of graphene (SLG) by mechanical stacking (Nottbohm, C. T., Turchanin, A., Beyer, A., Stosch, R. & Gölzhäuser, A. Mechanically Stacked 1-nm-Thick Carbon Nanosheets: Ultrathin Layered Materials with Tunable Optical, Chemical, and Electrical Properties. *Small* 7, 874-883, (2011)) on oxidized silicon wafers. The SLG have been grown by low-pressure chemical vapor deposition (CVD) of methane on copper foils (Li, X. S. et al. Large-area synthesis of high-quality and uniform graphene films on copper foils. *Science* 324, 1312-1314, (2009)). The chemically active amino groups of the $NH_2$-CNMs are located in these heterostructures in close vicinity to the graphene layers.

Figure 2:
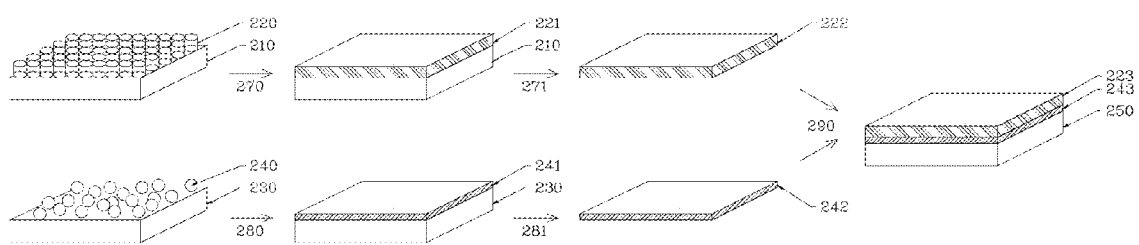
FIG. 2 is a scheme of an exemplary heterostructure assembly.

FIG. 2 shows a scheme for a method of manufacture of the $NH_2$-CNM/SLG heterostructures on the oxidized silicon wafers. This $NH_2$-CNM/SLG heterostructure serves as a non-limiting example of the heterostructure of the present disclosure as shown in FIG. 1. The method presented in FIG. 2 comprises two parallel routes including the fabrication of free-standing (i) $NH_2$-CNM 222 and (ii) SLG 242, which is finalized by the mechanical stacking (layer-by-layer assembly 290) of the $NH_2$-CNM sheets and of the SLG into the vertical vdW heterostructure. To this end, the $NH_2$-CNM sheets 221 have been prepared from self-assembled monolayers (SAMs) of 4'-nitro-1,1'-biphenyl-4-thiol 220 on Au/mica substrates 210 by electron irradiation (100 eV, 60 mC/$cm^2$) resulting in the lateral crosslinking of the biphenyl molecules (Turchanin, A. et al. Molecular mechnisms of electron-induced cross-linking in aromatic SAMs. *Langmuir* 25, 7342-7352, (2009)) and the conversion of the terminal nitro groups into amino groups 270. See, Eck, W. et al. Generation of surface amino groups on aromatic self-assembled monolayers by low energy electron beams—A first step towards chemical lithography. *Advanced Materials* 12, 805-808, (2000). The $NH_2$-CNM 221 is then released (271) from the Au/mica substrate 210 and transferred.

The SLG 241 have been grown by low-pressure chemical vapor deposition of methane 240 on a Cu substrate 230. Li, X. S. et al. Large-area synthesis of high-quality and uniform graphene films on copper foils. *Science* 324, 1312-1314, (2009). Annealing 280 yields a single layer of graphene 241 on the Cu substrate 230. The SLG is then released and transferred 281. The grown $NH_2$-CNM and SLG have been stacked by a layer-by-layer assembly of the heterostructure 290 on an oxidized highly doped silicon wafer by using the poly(methyl methacrylate) (PMMA) assisted transfer (Turchanin, A. et al. One nanometer thin carbon nanosheets with tunable conductivity and stiffness. *Advanced Materials* 21, 1233-1237, (2009); Pirkle, A. et al. The effect of chemical residues on the physical and electrical properties of chemical vapor deposited graphene transferred to $SiO2$. *Applied Physics Letters* 99, 122108, (2011)). In the formed heterostructure (see FIG. 2, right, formed of the Si/$SiO_2$ substrate 250, the single layer of graphene in the heterostructure assembly 243 and the $NH_2$-CNM in the heterostructure assembly 223), amino groups of the NH$_2$-CNMs are in close vicinity to the graphene layer, as they are separated from the surface of the graphene layer by an only about 1 nm thick dielectric sheet of cross-linked biphenylthiols. Turchanin, A. et al. One nanometer thin carbon nanosheets with tunable conductivity and stiffness. *Advanced Materials* 21, 1233-1237, (2009). The carbon nanomembranes can further be flexibly chemically functionalized for various applications. Zheng, Z. et al. Janus Nanomembranes: A Generic Platform for Chemistry in Two Dimensions. *Angewandte Chemie-International Edition* 49, 8493-8497, (2010); Turchanin, A. et al. Molecular self-assembly, chemical lithography, and biochemical tweezers: A path for the fabrication of functional nanometerscale protein arrays. *Advanced Materials* 20, 471-477, (2008).

Figure 3:
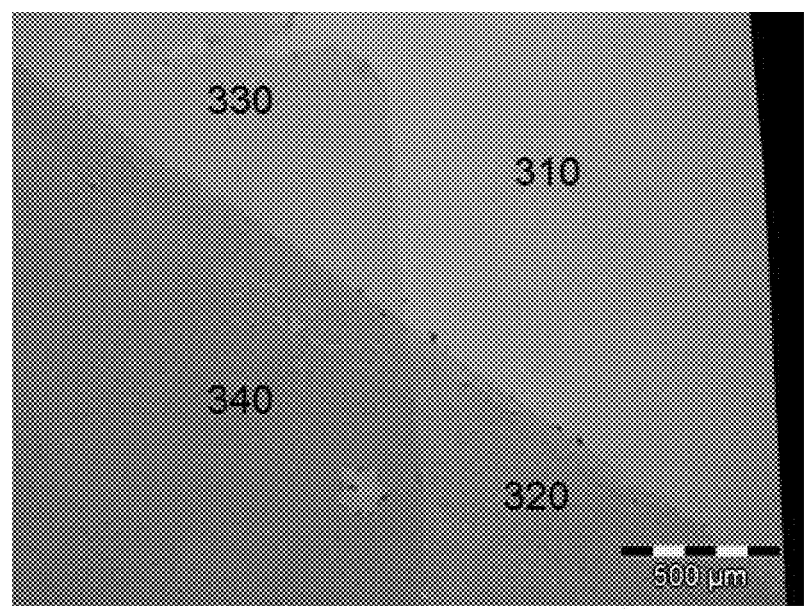
FIG. 3 is an optical microscope image of an NH$_2$-CNM/SLG heterostructure on an oxidized silicon wafer.

FIG. 3 shows an optical microscope image of a large area NH$_2$-CNM/SLG heterostructure fabricated on an oxidized (oxide thickness about 300 nm) silicon wafer. A large area heterostructure can be defined as a few mm in dimension. Four different regions can clearly be recognized in this image corresponding to the oxidized silicon wafer 310 and the areas with SLG 320, NH$_2$-CNM 330, and NH$_2$-CNM/SLG heterostructure 340. As expected for the dielectric NH$_2$-CNM, (Nottbohm, C. T., Turchanin, A., Beyer, A., Stosch, R. & Gölzhäuser, A. Mechanically Stacked 1-nm-Thick Carbon Nanosheets: Ultrathin Layered Materials with Tunable Optical, Chemical, and Electrical Properties. *Small* 7, 874-883, (2011)) its optical contrast appears lower in comparison to the well-conducting SLG. Blake, P. et al. Making graphene visible. *Applied Physics Letters* 91, 063124, (2007).

Figure 4A:
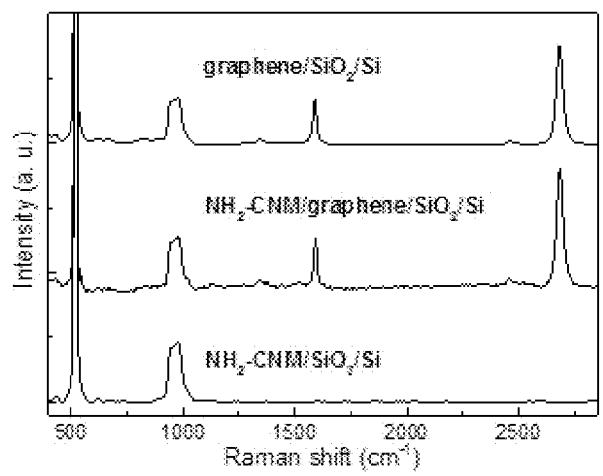
FIGS. 4A and 4B show Raman and XPS spectra of NH$_2$-CNMs, a SLG and an NH$_2$-CNM/SLG heterostructure.

Raman Spectroscopy and X-ray Photoelectron Spectroscopy (XPS) of the Heterostructure Raman spectroscopy has been employed at ambient conditions to characterize the graphene in different areas of this sample. As seen from FIG. 4A, the intensity ratios between the characteristic D-peaks and G-peaks of bare graphene and graphene integrated into the heterostructure are similar, which demonstrates that no additional structural defects are introduced into the SLG upon stacking the NH$_2$-CNM layer on the top of the SLG. Due to the disordered nature of the NH$_2$-CNM layer and its monolayer thickness (about 1 nm), the NH$_2$-CNM layer does not contribute to the measurable Raman intensity in this spectral range at the used experimental conditions. Nottbohm, C. T., Turchanin, A., Beyer, A., Stosch, R. & Gölzhäuser, A. Mechanically Stacked 1-nm-Thick Carbon Nanosheets: Ultrathin Layered Materials with Tunable Optical, Chemical, and Electrical Properties. *Small* 7, 874-883, (2011).

Figure 4B:
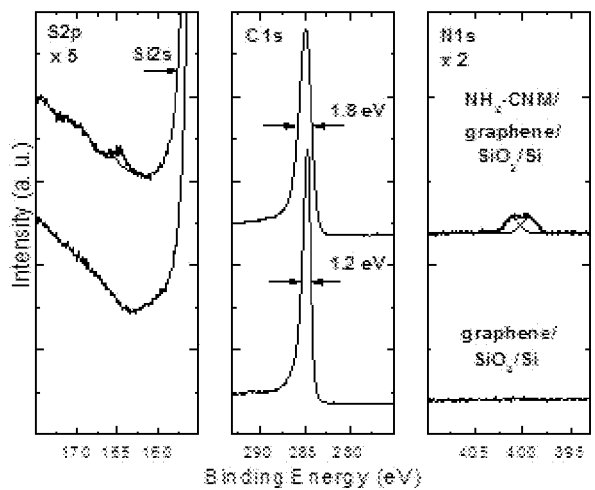

FIG. 4B presents high resolution XPS spectra of the core level S2p, C1s and N1s electrons of the heterostructure and the bare graphene regions. Due to the presence of the NH$_2$-CNM layer, the S2p and N1s signals are clearly detected for the heterostructure region, in which also an increase by 0.6 eV of the C1s FWHM value in comparison to the bare graphene is detected. The N1s signal is composed of two components at 399.3 eV and 401.2 eV, which are characteristic for pristine (—NH$_2$) and protonated (—NH$_3^+$) amino groups (Eck, W. et al. Generation of surface amino groups on aromatic self-assembled monolayers by low energy electron beams—A first step towards chemical lithography. *Advanced Materials* 12, 805-808, (2000)), respectively. As determined from attenuation of the substrate Si 2p signal (not shown) for the heterostructure and for the bare graphene, the NH$_2$-CNM layer contributes as expected with about 1.1 nm to the heterostructure thickness.

Thus, based on the spectroscopy characterization (Raman spectroscopy and XPS) it was demonstrated that via the fabrication of the NH$_2$-CNM/SLG heterostructures terminal amino groups are brought in close vicinity of the SLG without destroying the structural quality of the SLG. The person ordinarily skilled in the art will be aware that comparable results will be achieved with other examples of a carbon nanomembrane, other examples of the functionalization of the carbon nanomembrane and other examples of a carbon layer.

Figure 5A:
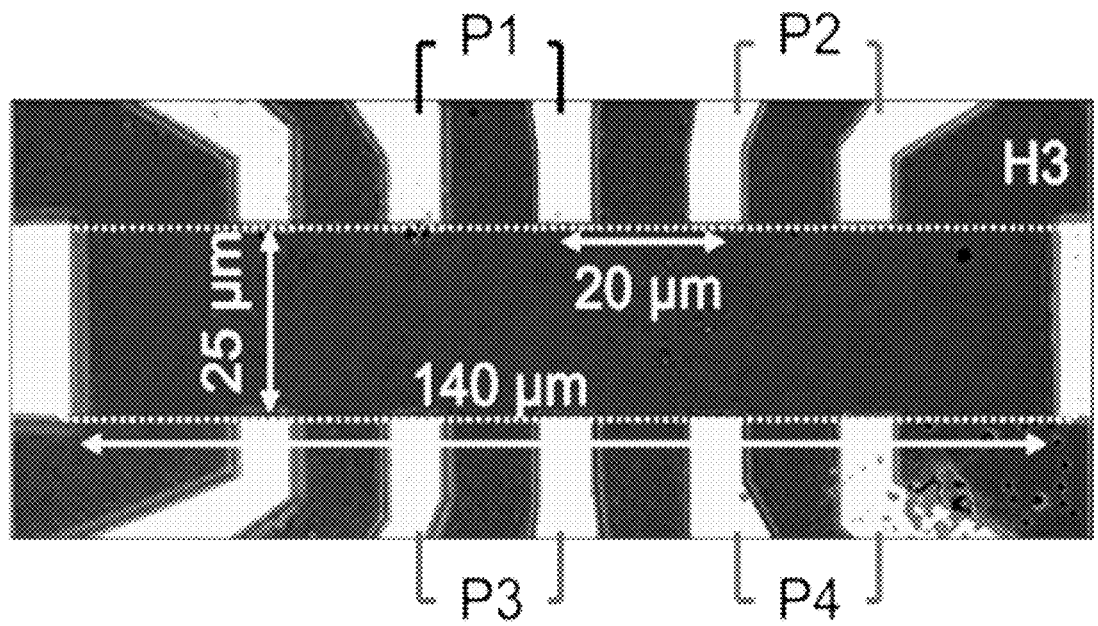
FIGS. 5A, 5B and 5C show electric transport measurements of bare graphene (G) and heterostructure (H) electric field devices.
Figure 5B:
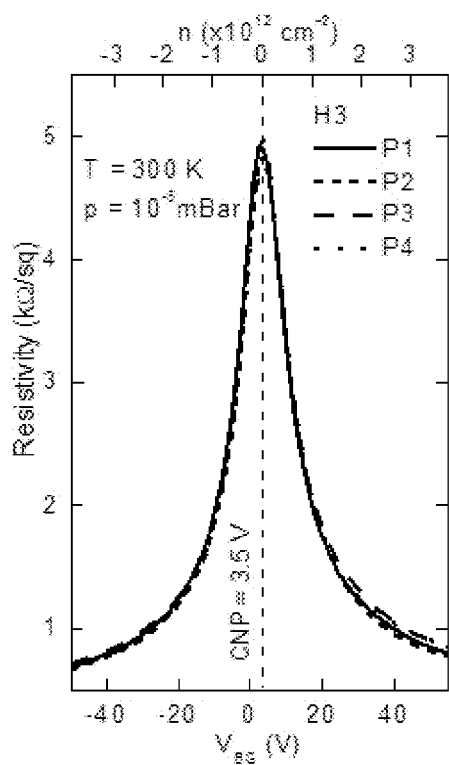

Electric and Electromagnetic Transport Measurements of the Heterostructure Device Four-point measurements have been performed to study the transport characteristics of the SLG integrated into the heterostructure devices and compare the transport characteristics of the heterostructure devices with the transport characteristics of bare graphene. To this end, a batch of large-area (140 µm×25 µm) Hall bar devices with several side contacts (see FIG. 5A was fabricated from the same CVD grown SLG placed on an oxidized silicon wafer. Then the wafer was sliced and a half of bare devices was directly examined, whereas on top of the second half a large-area NH$_2$-CNM layer was transferred to obtain the heterostructure devices. In these devices, the NH$_2$-CNM covers both graphene areas and gold wiring with the bonding pads. FIG. 5A presents an optical microscope image of one of the heterostructure devices. FIG. 5B presents room temperature (RT) electric-field effect measurements as a function of back-gate voltage, $U_{BG}$, at four different side contacts of the device (see FIG. 5A, P1-P4). As can be seen, the electrical characteristics are homogeneous on an area of about 3500 µm$^2$. By keeping this heterostructure device in high vacuum (about 10-5 mbar) at RT a shift of the graphene charge neutrality point (CNP) from initially 10 V to 3.5 V after pumping for 18 hours was observed. Since possible contaminations, trapped between the SLG and the silicon oxide substrate and/or between the SLG and the NH$^2$-CNM layer, cannot be removed by this treatment, this shift is attributed to desorption of the environmental adsorbates or the remaining rests of the transfer medium from the outer surface of the heterostructure device.

Figure 5C:
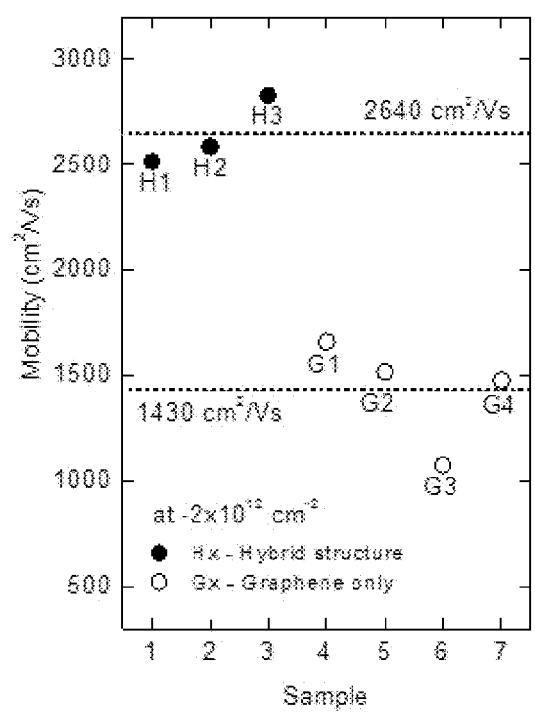

A difference is observed in the mobility data of the heterostructure (H) type devices and bare graphene (G) type devices. Prior to the measurements, all samples were kept at least for two hours in high vacuum (about 10-5 mbar, RT). For a hole concentration of 2×10$^{12}$ cm$^{-2}$ (see FIG. 5C) the mobility of the G-devices is µ=1000-1600 cm$^2$/Vs, whereas the Hdevices have a mobility increased by about 80%, µ=2500-2640 cm$^2$/Vs. As at low carrier concentrations graphene mobility is limited by scattering on the charged impurities, (Mayorov, A. S. et al. How Close Can One Approach the Dirac Point in Graphene Experimentally? *Nano Letters* 12, 4629-4634, (2012)) higher mobility values for the Hdevices in comparison to the G-devices correlate with the lower residual carrier concentrations.

Figure 6:
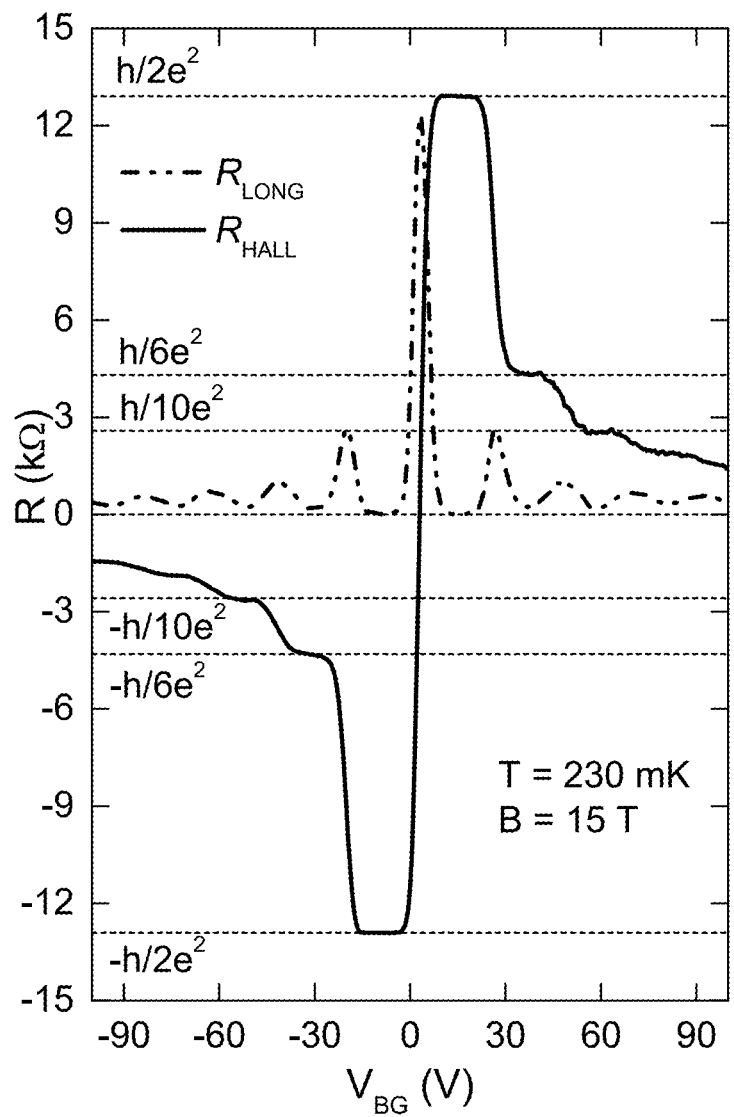
FIG. 6 shows magneto-transport measurements of the heterostructure device at low temperature (H3, T=230 mK).

Further, it was demonstrated that at low temperatures the magneto-transport properties of the heterostructure devices comprising the heterostructures of this disclosure reproduce very well the quantum mechanical phenomena attributed to SLG, see FIG. 6. At a high magnetic field, the quantum Hall effect (QHE) in device H3 appears as a sequence of plateaus accompanied by the longitudinal resistance oscillations.

Thus, the magneto-transport measurements demonstrate that the intrinsic quality of graphene is preserved in the fabricated NH$_2$-CNM/SLG van der Waals heterostructure device and that the chemical functionalization of SLG has been achieved in a non-destructive manner.

Electric Field Response of the Electric-Field Devices in Water

To test the heterostructure devices for possible sensor applications, the heterostructure devices of the present disclosure were exposed to Millipore water at ambient conditions and their electrical response was measured. The $NH_2$-CNM sheets insulate the underlying graphene layer from water (Turchanin, A. & Gölzhäuser, A. Carbon nanomembranes from self-assembled monolayers: Functional surfaces without bulk. *Progress in Surface Science* 87, 108-162, (2012)) and therefore the graphene resistivity can only be affected by a change in the electrostatic environment at the $NH_2$-CNM/water interface. Water droplets were placed on the heterostructure device area using a micropipette, and after the measurements the water droplets were blown away by purging with nitrogen. FIG. 7A shows the ambipolar electric field effect of the same device comprising a heterostructure at ambient conditions and in water. The presence of water results in n-doping of graphene and a shift of the CNP by about 27 V.

FIG. 7B shows the corresponding dynamic response of the heterostructure device resistivity acquired by four point measurements with a direct current of 1 µA and $U_{BG}$=0 V. Just after placing the first water droplet (first arrow from left), which only partially covered the heterostructure device area, a noticeable and rapid change of the resistivity was detected. After the full coverage with water (second arrow from left) a giant increase by at least 400% of the graphene resistivity was measured, which corresponds to a decrease of the charge carrier concentration in agreement with the ambipolar electric-field effect presented in FIG. 7A. Blowing the droplet away (right arrow) results in a fast recovering of the resistivity to its initial value of about 1.6 kΩ/sq. Some instability of the resistivity signal in water was caused by the evaporation and droplet movement, which was observed in an optical microscope.

Thus, the intrinsic electronic properties of carbon layers, e. g., high electrical charge mobility, strong ambipolar electric field effect and high thermal conductivity, are not disturbed and can be preserved upon functionalization. The carbon nanomembrane can serve as an effective encapsulation layer improving the electric transport. The preservation of the intrinsic electronic quality of the pristine carbon layers opens up broad avenues for use of the heterostructure of the present invention in carbon layer-based electronic devices, e. g., for engineering electronic devices for chemical and bio-sensing. The examples show a layer of graphene as the carbon layer but other carbon layers are also possible.

Chemical Sensors

Figure 8A:
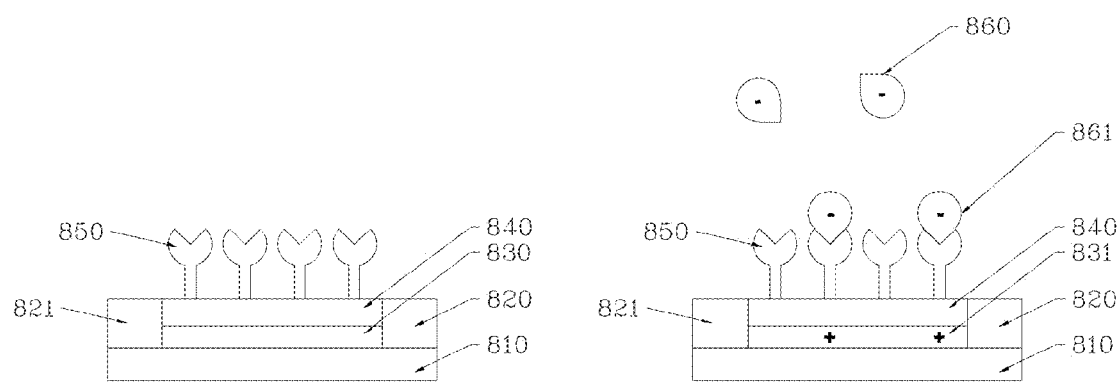
FIGS. 8A and 8B illustrate the operation principle of a graphene-based field-effect-transistor-sensor.

The heterostructures of the present disclosure can be employed in chemical sensors. One example of the heterostructure is shown in FIG. 8A. Charge transfer from an absorbate that shifts the transconductance between source 820 and drain 821 or in other words, the binding of a charged molecule, leads to the charge on the gate in the chemical sensors. As a consequence, the conductivity between the source and the drain is changed. FIG. 8A shows the gate oxide (e. g. $SiO_2$) 810 with graphene 830 and $NH_2$-CNM 840 functionalized with capture molecules 850 on top as well as the source 820 and the drain 821. On the right hand side, a negatively charged target molecule 860 binds to the capture molecule 850 to result in a charged target molecule bound to a capture molecule on the sensor surface 861. The layer of graphene is doped (+) 831.

Figure 8B:
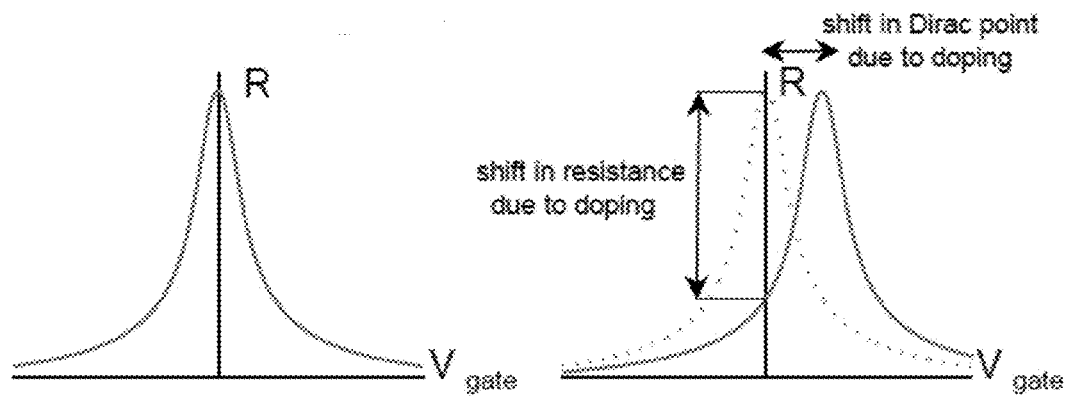

FIG. 8B shows the resistance of the chemical sensor as a function of gate voltage. The graphene, which consists of a single layer of $sp^2$ bound carbon atoms arranged in a honeycomb pattern, has a high, essentially infinite, surface to volume ratio. Any single atom that adsorbs to the surface of graphene has the potential to change the electronic properties of graphene.

Graphene is only one example for the use in chemical sensors. The person skilled in the art will be aware that other carbon layers may also be used because non-covalent functionalization by vdW forces works with every kind of carbon layer. The chemical sensor may be comprised in an electronic-fluidic sensor package. The specificity of detection may be provided by functionalization of sensor surfaces. Functionalization may be carried out with at least one of a fluorescent dye, a chelator, a protein, an antibody, an oligonucleotide, or a metallic nanoparticle.

Fullerene ($C_{60}$)-CNM Heterostructure

Figure 9:
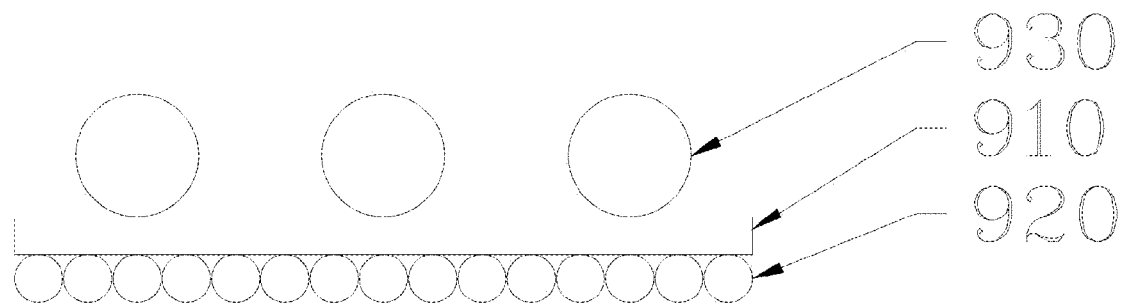
FIG. 9 is a schematic of a C$_{60}$-CNM heterostructure functionalized with Au-nanoparticles on the thiol-terminated CNM-side.

FIG. 9 shows a schematic of a Fullerene ($C_{60}$)-CNM heterostructure. The CNM 910 is functionalized with a thiol group and further functionalized by Au-nanoparticles 930 bound to the thiol-terminated side of the CNM 910. On the other side of the CNM 910, a layer of fullerene 920 is bound. On the side of the CNM 910 on which the layer of fullerene 920 is bound, the CNM may be functionalized with an amino group.

Helium Ion Microscopy of a Freestanding $C_{60}$-CNM Heterostructure

Figure 10:
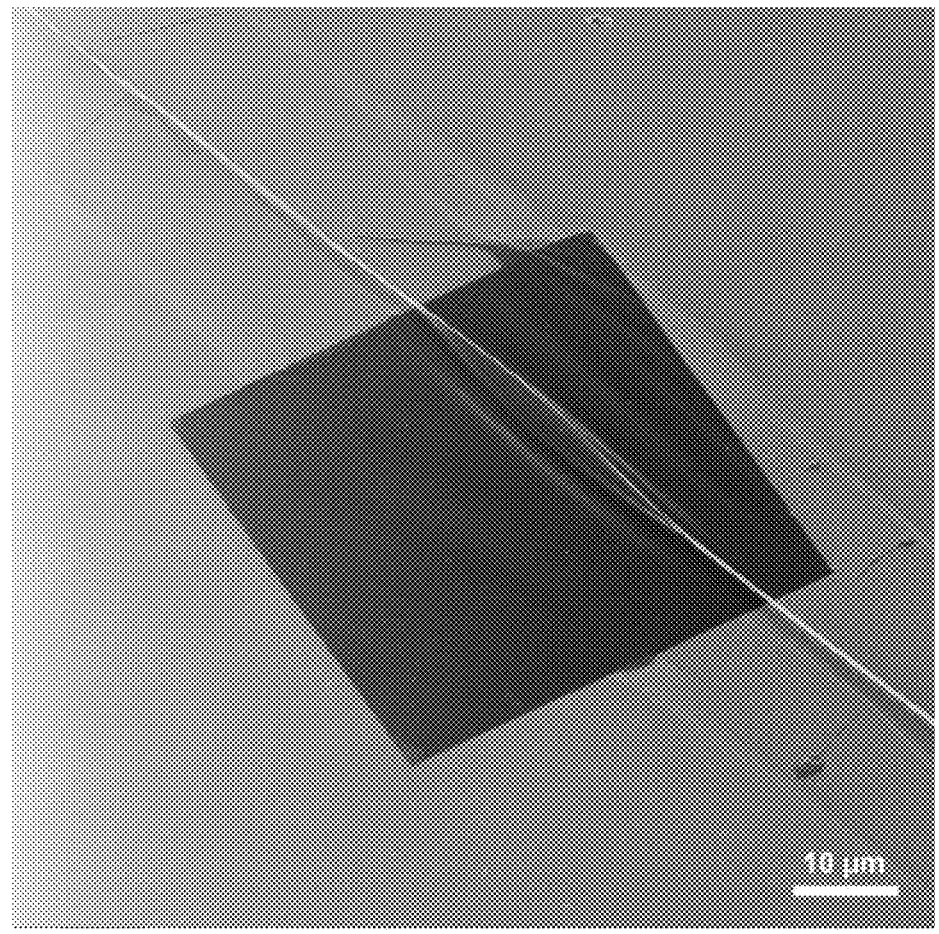
FIG. 10 is an HIM-image of a freestanding C$_{60}$-CNM heterostructure over an orifice with the dimension of 40×44 µm$^2$ on a Si substrate.

Helium ion microscopy (HIM) was employed to image the supported and free-standing $C_{60}$-CNM heterostructure. To this end, a $C_{60}$-CNM heterostructure was transferred onto a silicon substrate with an array of square shaped orifices (FIG. 10). An area with a fold in the membrane has been chosen in order to easier visualize the freestanding structure. A fold is clearly recognizable. The CNM provides the fullerene layer with mechanical stability, as the HIM image shows. A single layer of fullerene would otherwise not be mechanically stable.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

REFERENCE NUMERALS 110 carbon layer
120 carbon nanomembrane
210 Au/mica substrate
220 self-assembled monolayer (SAM) of 4'-nitro-1,1'-biphenyl-4-thiol
221 $NH_2$-CNM
222 $NH_2$-CNM released from substrate
223 $NH_2$-CNM in the heterostructure assembly
230 Cu substrate
240 methane deposited by chemical vapor deposition
241 single layer of graphene
242 single layer of graphene released from substrate
243 single layer of graphene in the heterostructure assembly
250 Si/$SiO_2$ substrate 270 electron irradiation resulting in the lateral crosslinking of the biphenyl molecules and the conversion of the terminal nitro groups into amino groups
271 release of NH$_2$-CNM released from substrate and transfer
280 annealing
281 release of single layer graphene and transfer
290 layer-by-layer assembly of the heterostructure
310 oxidized silicon wafer
320 single layer of graphene
330 NH$_2$-CNM
340 heterostructure: NH$_2$-CNM on a single layer of graphene
810 gate oxide (e.g. SiO$_2$)
820 source
821 drain
830 graphene
831 doped graphene
840 NH$_2$-CNM
850 capture molecule
860 charged target molecule
861 charged target molecule bound to a capture molecule on the sensor surface
910 CNM
920 layer of fullerene
930 Au-nanoparticle

The invention claimed is:

1. A heterostructure comprising:
at least one non-metallic carbon nanomembrane of cross-linked molecules of at least one carbon-containing compound, the non-metallic carbon nanomembrane being stacked on top of at least one carbon layer, and at least one surface of the non-metallic carbon nanomembrane being terminated with at least one functional group, which is separated from a surface of the carbon layer by the cross-linked molecules,
wherein the at least one non-metallic carbon nanomembrane has a thickness of 0.5 to 5 nm and the non-metallic carbon nanomembrane and the carbon layer have a combined thickness of 1 to 10 nm.

2. The heterostructure according to claim 1, wherein the carbon layer is a single layer of graphene or a single layer of fullerene.

3. The heterostructure according to claim 1, wherein the at least one functional group is selected from the group consisting of halogen atoms and carboxy, trifluoromethyl, amino, nitro, cyano, thiol, hydroxy or carbonyl groups.

4. The heterostructure according to claim 1, wherein the at least one functional group is an amino group.

5. The heterostructure according to claim 1, wherein the at least one surface of the carbon nanomembrane, which is terminated with at least one functional group, is further functionalized.

6. The heterostructure according to claim 1, wherein the at least one surface of the carbon nanomembrane, which is terminated with at least one functional group, is further functionalized by at least one of a fluorescent dye, a chelator, a protein, an antibody, an oligonucleotide or a metallic nanoparticle.

7. The heterostructure according to claim 6, wherein the fluorescent dye is tetramethylrhodamine or the chelator is ethylenediaminetetraacetate.

8. A sensor comprising:
a heterostructure comprising at least one non-metallic carbon nanomembrane of cross-linked molecules of at least one carbon-containing compound, the non-metallic carbon nanomembrane being stacked on top of at least one carbon layer, and at least one surface of the non-metallic carbon nanomembrane being terminated with at least one functional group, which is separated from a surface of the carbon layer by the cross-linked molecules,
wherein the at least one non-metallic carbon nanomembrane has a thickness of 0.5 to 5 and the at least one non-metallic carbon nanomembrane and the at least one carbon layer have a combined thickness of 1 to 10 nm.

9. The sensor according to claim 8, further comprising a microfluidic system fluidly connected to the sensor.

10. The heterostructure of claim 1, wherein the at least one non-metallic carbon nanomembrane is a substantially two-dimensional structure.

* * * * *